US00PP09487P

United States Patent [19]

Magee

[11] Patent Number: Plant 9,487

[45] Date of Patent: Mar. 26, 1996

[54] ILEX HYBRID VARIETY NAMED 'CONAF'

[75] Inventor: Jack M. Magee, Poplarville, Miss.

[73] Assignees: Jack Mitchell Magee, Poplarville, Miss.; Flowerwood Nsy Inc., Mobile, Ala.

[21] Appl. No.: 408,541

[22] Filed: Mar. 22, 1995

[51] Int. Cl.[6] ..... A01H 5/00

[52] U.S. Cl. ..... Plt./65

[58] Field of Search ..... Plt./65

[56] References Cited

U.S. PATENT DOCUMENTS

P.P. 8,792 6/1994 Fischer ..... Plt./65

P.P. 8,793 6/1994 Fischer ..... Plt./65

*Primary Examiner*—James R. Feyrer

[57] ABSTRACT

A new amd distinct variety of Ilex plant found as an openly pollinated seedling of Ilex Hybrid 'Mary Nell'. The new variety possesses an upright, pyramidal growth habit, flowers which produce functional pollen and ovaries, attractive orange-red fruit, unusual dull green foliage, and distinctly arranged leaf serrations.

2 Drawing Sheets

BACKGROUND OF THE INVENTION

This new variety was found as an openly pollinated seedling of Ilex Hybrid 'Mary Nell', an unpatented variety, maintained in the Evergreen Nursery at Poplarville, Miss. The seedling was found in May, 1989. The new and distinct Ilex Hybrid plant of this invention comprises a novel and valuable holly plant with an upright, pyramidal shape, attractive orange-red fruit, and unusual leaf serrations. As with the parent plant, the plant of this invention may be advantageously employed as a specimen appointment, in either formal or informal groupings, and is very attractive in mass plantings. The plant serves well in foundation plantings and is adapted for culture as a potted plant. This plant is responsive to pruning and training and may be used in forming attractive hedges and maintained without an excessive amount of care.

Asexual propagation of the new plant by cuttings has been under Mr. Magee's direction at the same location. Several generations of the new plant have been evaluated and the distinctive characteristics of the plant have remained stable.

SUMMARY OF THE INVENTION

The following are the most outstanding and distinguishing characteristics of this new cultivar when grown under normal horticultural practices in Poplarville, Miss.

1. Upright and pyramidal in nature.
2. Hardy to Zone 7.
3. Heat and drought tolerant.
4. Fast growth rate under normal fertilization and moisture conditions.
5. Tolerates most soils from moist to dry and from sand to clay.
6. Relatively pest resistant.
7. Very desirable in planters.
8. Makes a good hedge.
9. Easy to root from cuttings collected any time of year.
10. Flowers are perfect and can effectively pollinate other forms of Ilex.

11. Produces attractive orange-red fruit in the fall which persist into the winter and may result in bird visitation.
12. Has the ability to be sheared and trimmed to be kept within prescribed limits.
13. Mature leaves are a dull green color with attractive spines.

DESCRIPTION OF THE DRAWINGS

This new Ilex Hybrid variety is illustrated by the accompanying photographic prints in which.

Figure 1:
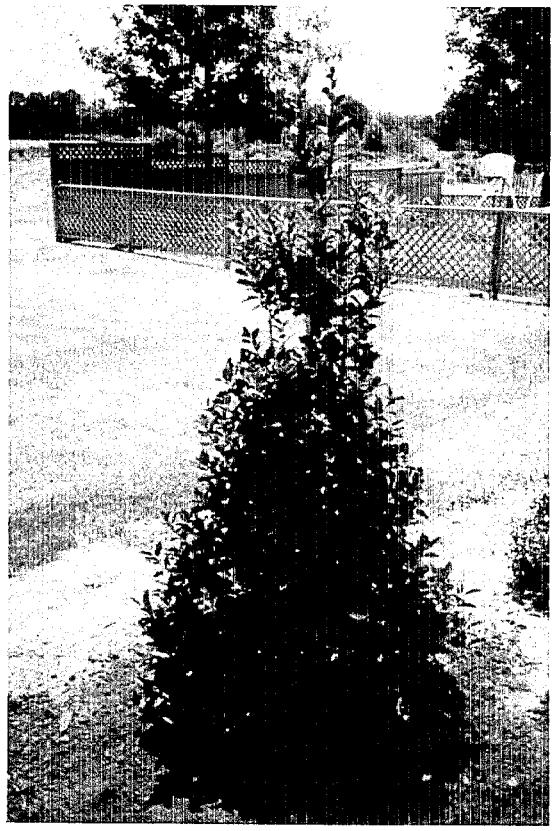
FIG. 1 discloses the upright pyramidal shape of the new variety.
Figure 2:
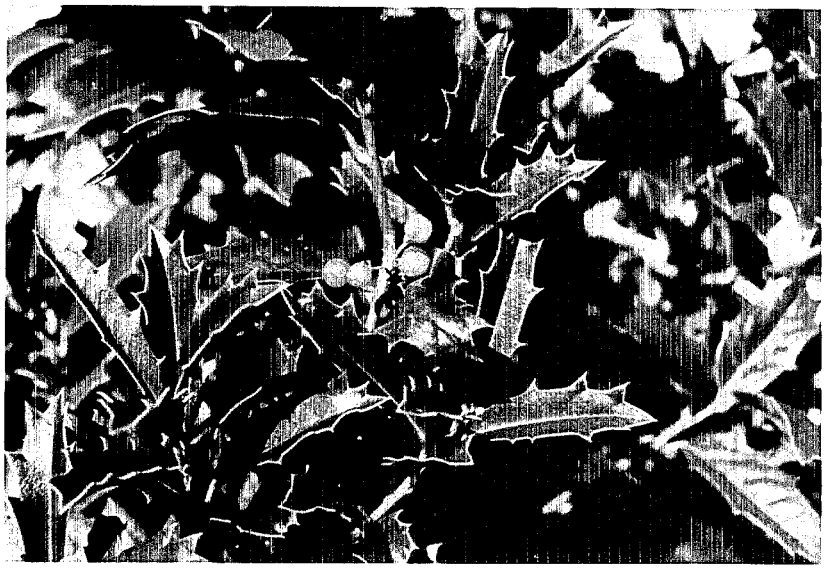
FIG. 2 shows a close-up view of the attractive orange-red fruit and mature foliage of the new variety.
Figure 3:
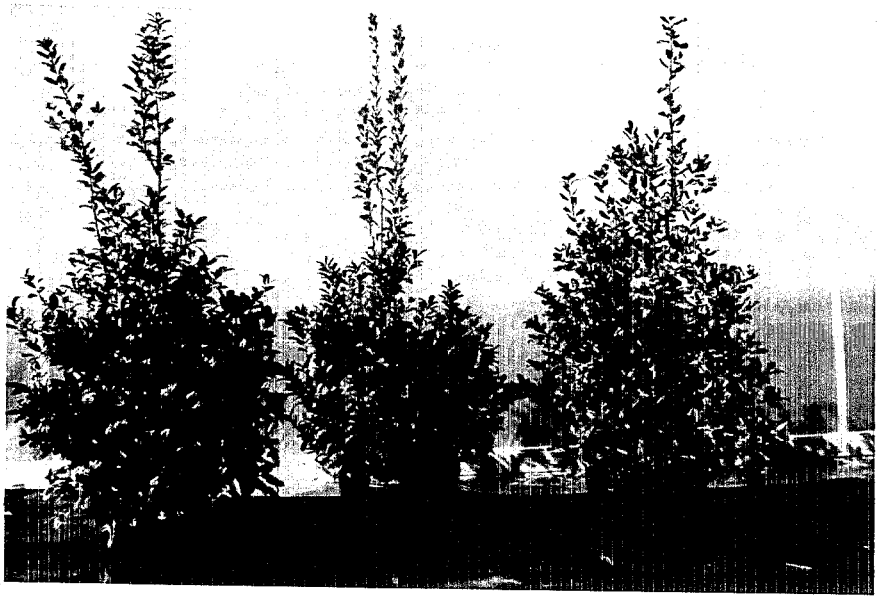
FIG. 3 is a side-by-side photograph of (from left to right) the parent plant Ilex Hybrid 'Mary Nell', the new variety, and Ilex Hybrid 'Nellie R. Stevens'. The mid-winter photograph shows the new variety's upright pyramidal shape and slightly lighter mature foliage color.
Figure 4:
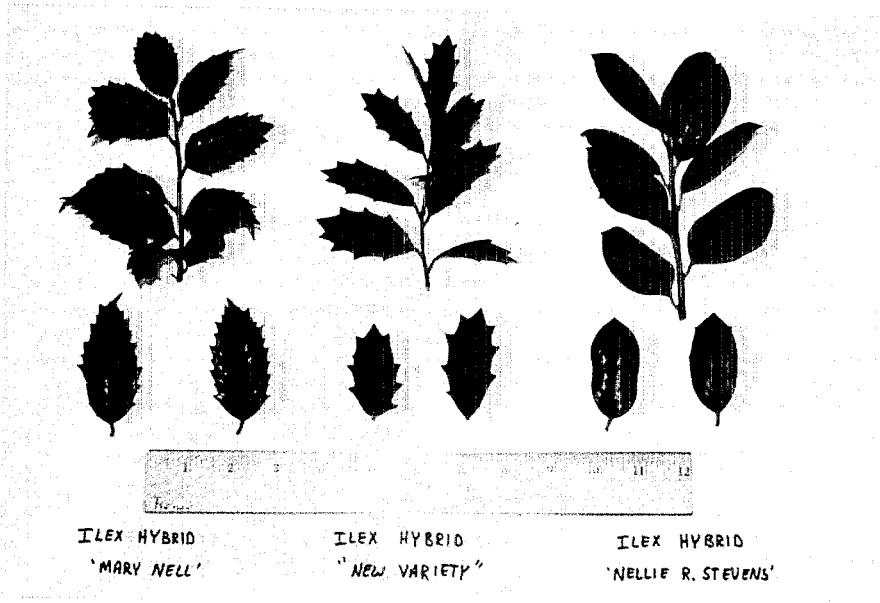
FIG. 4 is also a side-by-side photograph illustrating the leaf shapes and sizes of (from left to right) the parent plant Ilex Hybrid 'Mary Nell', the new variety, and Ilex Hybrid 'Nellie R. Stevens'. Also evident is the less glossy leaf of the new variety compared to the other hollies.

The colors shown are as true as is reasonably possible to obtain by conventional photographic procedures. The colors of the various plant parts are defined with reference to The Royal Horticultural Society Colour Chart. Description of colors in ordinary terms are presented where appropriate for clarity in meaning.

BOTANICAL DESCRIPTION OF THE PLANT

The following is a detailed description of the new variety of Ilex based on my observations made of plants grown in wholesale commercial production practices, in greenhouses, and established landscape plantings in Poplarville, Miss.

| Distinctive Characteristics: | | | |
|---|---|---|---|
| Characteristic | 'Conaf' | 'Mary Nell' | 'Nellie R. Stevens' |
| Height (Mature) | 15–20' | 15–25' | 15–25' |
| Width (Mature) | 12–15' | 12–15' | 12–15' |
| Leaf Length | 2–3 ½" | 2 ⅝–3 ½" | 2 ¼–3" |
| Leaf Width | 1 ⅛–1 ⅝" | 1 ⅛–1 ¾" | 1–1 ½" |
| Leaf Color (Mature) | Closest to Green Group 139A | Green Group 139A | Green Group 139A |
| Leaf Glossiness (Mature) | Dull | Very glossy | Glossy |
| Leaf Shape | Ovate to lanceolate | Ovate to broadly lanceolate | Ovate |
| Leaf Spines (Pairs) | 3–5 | 9–11 | 2–3 |
| Terminal Spines | 3 | 1 | 1–3 |
| Fruit Color | Orange-Red Group 33A | Red Group 40A | Orange-Red Group 33A |
| Flowers Sex | Male & Female | Female only | Female only |
| Leaf Base | Obtuse | Obtuse | Obtuse |
| Mature Shape | Upright | Upright | Upright Pyramidal |
| Hardiness | Zone 7 | Zone 7 | Zone 6 |

The parent plant of the new variety, 'Conaf' is Ilex 'Mary Nell' which originated from a controlled cross made in 1962 by Joe McDaniel at Tom Dodd Nurseries in Semmes, Ala. The female parent was *Ilex* (*cornuta* 'Burfordii'×*pernyi*) 'Red Delight'. A selection of Henry Hohman, Kingsville Nurseries, Kingsville, Md. The male parent was *Ilex latifolia*. Ilex 'Mary Nell' was named in 1981 by Thomas H. Dodd, Jr. after Joe McDaniel's wife.

Ilex Hybrid 'Nellie R. Stevens', which is very popular in the industry, is a hybrid between *Ilex aquifolium* and *Ilex cornuta*. It was released by G. A. Van-Lennep, Jr., St. Michael, Md. in 1954. It is named for the owner, Nellie R. Stevens, Oxford, Md. This non-patented plant is comparable to the new plant, however, there are many differences. The flowers of the new variety contain male and female parts which are both functional compared to the Ilex 'Nellie R. Stevens' and Ilex 'Mary Nell' flowers which have viable ovaries but the anthers produce no pollen. The new variety also has more spines, 7–9 (pairs) compared to 2–3 (pairs) and less glossy mature leaves.

It is from the openly pollinated seedlings of the Ilex 'Mary Nell' plant that I found the new plant. This new variety will be sold under the trademark Oak Leaf.

Classification:

*Botanic.*—Ilex Hybrid 'Conaf'.

Form: Upright and pyramidal.

Texture: Medium to coarse.

Height: 15–20'.

Width: 12–15'.

Growth habit: Upright and pyramidal. Fast growth rate under normal fertilizaton and moisture conditions.

Foliage: Alternate, simple, evergreen, ovate to lanceolate, and vary in size from 2–3½" long and 1⅛– 1⅝" wide. The margins are serrate with 3–5 pairs of prominent spines. The spines vary in length and width from ⅛ to 5/16 " on the plant but spines on each leaf are almost uniform in size. The apex is acute with 3 terminal spines and the base is obtuse. The petiole is ¼–⅜" long. Mid-veins and laterals are impressed on the upper leaf surface and the mid-veins are prominent on the underside. The upper surface of the immature leaves are semi-glossy, glabrous, and are Yellow-Green Group 144A. The lower surface of the immature leaves are Yellow-Green Group 144A and matte. As the leaves mature they become less glossy and the upper surface becomes closest to Green Group 139A and the lower leaf surface becomes Yellow-Green Group 146C. This mature leaf color persists through the winter. Although the mature leaf color of the new variety is closest to Green Group 139A, which is also the color of the parent plant, it appears to be a shade lighter when viewed in full sun. This could be due to the dull leaf surface of the new variety.

In 1992, the date of initial spring growth was March 10, in Poplarville, Miss. After the initial spring flush there was almost continuous growth until fall ending October 22, also in Poplarville, Miss. This growth pattern was identical to the parent plant. When grown in full sun, the internode length of the plant is ½–¾" compared to ⅝ –1¼" for the parent plant. When grown in light shade the internode length is ¾–1". As would be expected either plant growth in the shade results in a taller less dense plant with larger leaves.

The average length of terminal growth of the initial spring flush is about 12" for a plant in full sun and 14" when grown in shade. After this initial flush we normally trim the plant lightly and the plant then continues to grow about 8" until we trim it a second time in the early fall. The fall growth of about 10" then hides the cut limbs. We finish in the fall with a three gallon plant about 34" tall and 20" wide. I have not noticed a difference in vigor between this plant and the parent. Although there are many variables involved it should take about 8–10 years for this plant to reach a mature height of 15–20' tall and width 12–15'. In the landscape little or no pruning is necessary to produce an upright pyramidal shrub in full sun. In shade, however, some trimming may be needed to produce the same effect.

Stems: The young shoots and petioles are Yellow-Green Group 144A, glabrous, and matte. After one or more years the stems are generally Green-Brown Group 199C, glabrous and rugose. The pith is solid and uniform.

Flowers: Perfect, small, creamy yellow, inconspicous, slightly fragrant, borne on previous season's growth from March to May. Buds are globular, Yellow-Green Group 144A, and without foliaceous appendages. Flowers are clustered in the leaf axils and are 4-merous. Unbranched pedicels are about ¼" long and Yellow-Green Group 144A. The four ovate petals are arranged regularly, united at the base, and imbricate in bud. The ovary protrudes from the receptacle and is Green Group 143A. There are four stamen with immature anthers White Group 155D. As the anthers mature and pollen is released the color becomes Yellow Group 3C. Blooms are small to medium in size, Yellow Group 2D, ⅜" diameter, and last on the plant in the garden 2–4 days.

Fruit: Drupaceous, globose, ¼–⅜" diameter, borne fasciculate with 2–15 fruits on short unbranched pedicels ¼" long. Each fruit contains 4 pyrenes. Matures to Orange-Red Group 33A in mid—November in Poplarville, Miss. and persists into the winter. Normally fruit set is heavy.

Culture: Grows well in a wide range of conditions and tolerates sun to part shade. Grows in nearly any soil type, from moist to very dry and sand to clay. Responds well to mulching and medium applications of fertilizer, prefers ph 5 to 6.5. Little pruning is needed. Can be sheared. Propagated with semi-hardwood cutting any time of the year.

I claim:

1. A new and unique variety of Ilex plant named Ilex Hybrid 'Conaf' as herein shown and described, is characterized by its upright and pyramidal growth habit, perfect flowers which produce an abundance of pollen, dull mature leaves, distinctly arranged leaf serrations, orange-red fruit, fast growth rate, resistance to pests, and tolerance of heat, drought, and soil type.

* * * * *